US012611532B2

(12) United States Patent
Dombrowski et al.

(10) Patent No.: US 12,611,532 B2
(45) Date of Patent: Apr. 28, 2026

(54) CLEANING CAP FOR MEDICAL IMPLEMENT

(71) Applicant: Solventum Intellectual Properties Company, Maplewood, MN (US)

(72) Inventors: Alan R. Dombrowski, Woodbury, MN (US); Adam S. Troness, Dellwood, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 1132 days.

(21) Appl. No.: 17/628,675

(22) PCT Filed: Jul. 14, 2020

(86) PCT No.: PCT/IB2020/056625
§ 371 (c)(1),
(2) Date: Jan. 20, 2022

(87) PCT Pub. No.: WO2021/014274
PCT Pub. Date: Jan. 28, 2021

(65) Prior Publication Data
US 2022/0313976 A1 Oct. 6, 2022

Related U.S. Application Data

(60) Provisional application No. 62/878,124, filed on Jul. 24, 2019.

(51) Int. Cl.
*A61M 39/16* (2006.01)
*A61M 5/31* (2006.01)
*A61M 39/20* (2006.01)

(52) U.S. Cl.
CPC ... *A61M 39/162* (2013.01); *A61M 2005/3104* (2013.01); *A61M 2039/205* (2013.01)

(58) Field of Classification Search
CPC ........ A61M 39/162; A61M 2005/3104; A61M 2039/205; A61M 39/16
See application file for complete search history.

(56) References Cited

U.S. PATENT DOCUMENTS

| | | | | |
|---|---|---|---|---|
| 4,432,764 A | * | 2/1984 | Lopez | A61M 39/20 |
| | | | | 604/905 |
| 4,597,758 A | * | 7/1986 | Aalto | A61M 39/20 |
| | | | | 604/263 |

(Continued)

FOREIGN PATENT DOCUMENTS

| | | |
|---|---|---|
| CN | 203494034 U | 3/2014 |
| CN | 107198823 B | 9/2023 |

(Continued)

OTHER PUBLICATIONS

International Search Report for PCT International Application No. PCT/IB2020/056625, mailed on Aug. 13, 2020, 4 pages.

*Primary Examiner* — Bradley J Osinski

(57) ABSTRACT

The disclosed cap for attachment to a medical implement having a male protrusion includes a movable plunger and a depth stop for limiting the translational movement of the plunger. Typically, the cap will include a cleaning solution that is displaced by the movable plunger. The depth stop controls of the displacement of the plunger such that a consistent air-tight seal is made between the surface of the plunger and a surface of the male luer.

17 Claims, 6 Drawing Sheets

(56) References Cited

U.S. PATENT DOCUMENTS

| 9,999,471 | B2 * | 6/2018 | Rogers | A61M 39/16 |
|---|---|---|---|---|
| 2012/0039765 | A1 | 2/2012 | Solomon | |
| 2013/0006194 | A1 | 1/2013 | Anderson | |
| 2013/0019421 | A1 * | 1/2013 | Rogers | A61M 5/315 |
| | | | | 15/104.93 |
| 2013/0190713 | A1 | 7/2013 | Ranalleta | |
| 2014/0148781 | A1 | 5/2014 | Tekeste | |
| 2018/0369561 | A1 | 12/2018 | Coyle | |

FOREIGN PATENT DOCUMENTS

| EP | 2075032 B1 | 4/2011 |
|---|---|---|
| JP | 2002-210008 | 7/2002 |
| WO | WO 2018-106508 | 6/2018 |

* cited by examiner

CLEANING CAP FOR MEDICAL IMPLEMENT

CROSS REFERENCE TO RELATED APPLICATIONS

This application is a national stage filing under 35 U.S.C. 371 of PCT/IB2020/056625, filed Jul. 14, 2020, which claims the benefit of U.S. Provisional Application No. 62/878,124, filed Jul. 24, 2019, the disclosures of which are incorporated by reference in their entirety herein.

BACKGROUND

The present application relates to a cleaning cap for a medical implement having a male protrusion, and more particularly a cleaning cap having a movable plunger.

A male luer connector is a fitting for making fluid-tight connections between medical devices such as syringes, ports, or fluid lines like catheters, drains or intravenous (IV) lines. Male luers include a tapered male protrusion defining a lumen, where the protrusion extends out from a sleeve or collar that has internal threads on an inner wall of the sleeve or collar.

Typically, medical devices are connected and disconnected frequently from the male luer. While disconnected, the exposed end of the male luer can become contaminated. One conventional solution for protection of a male luer is with a disinfecting cap containing a cleaning solution, which can disinfect the male luer connector. Cleaning caps may also include a movable plunger, in which cleaning solution may bathe the male luer when it is forced from an inner cavity of the cap by translational movement of the plunger

SUMMARY

The disclosed cap for attachment to a medical implement having a male protrusion includes a movable plunger and a depth stop for limiting the translational movement of the plunger. Additionally, the plunger includes a sealing interface surface for creating an air-tight seal between the plunger and the top surface of the male protrusion. Typically, the cap will include a cleaning solution that is displaced by the movable plunger.

Male luers may have molding deformities on the top surface of the male protrusion, which may prevent an air-tight seal between the sealing interface surface of the plunger and the top surface of the male luer. These deformities may include mold flash which can occur along the inner lumen surface of the male protrusion and project outwards, thus preventing a complete seal from forming against the plunger. A poor seal may allow cleaning solution to ingress into the lumen of the male luer. Male luer also have variances in length of the male protrusion and sleeve depths. This allows caps to be attached to the luers and have varying plunger displacements. Finally, there is no "hard" stop of the plunger in the cap at the end of travel after the cap is attached. Thus, when the cap is attached to a male luer of a syringe, the plunger may be displaced away from the top surface of the male protrusion when sufficient pressure is built up within the syringe cavity. This pressure can occur if the syringe plunger is pressed. As such, without a mechanism for preventing displacement of the plunger from the top surface of the male protrusion when the syringe is under pressure, the sealing ability of the cap may be compromised and fluid may escape the lumen of the syringe male luer and be expelled outside of the disinfecting cap.

The disclosed cap with a depth stop provides for control of the depth of the male luer into the cap, and therefore control of the displacement of the plunger. The depth stop ensures that a consistent air-tight seal is made between the surface of the plunger and a surface of the male luer across all male luers. Additionally, the plunger may include a male luer interface surface configured to accommodate molding deformities on the top surface of the male luer.

In one embodiment, a cleaning cap for a medical implement having a male protrusion comprises a housing and a plunger disposed within the inner cavity of the housing. The housing has an inner wall that defines an inner cavity and an opening. The housing has a distal end and a proximal end. The opening to the inner cavity is at the proximal end of the housing. The plunger is. The plunger comprises a rearward end facing the opening, a forward end opposite the rearward end. The plunger is movable between a first position and a second position. Within the inner cavity of the housing is at least one depth stop. At the first position, the plunger is free to move translationally away from the opening, and at the second position the plunger abuts the depth stop preventing translational movement of the plunger away from the opening.

In one embodiment, the cleaning cap may include one or more depth stops. A first depth stop may include at least one inwardly extending abutment features that may extend from an inner wall of the cap towards the inner cavity proximate a distal end of a cap housing. A second depth stop may include a step proximate a medial portion of the housing that may extend from the inner wall towards the inner cavity. A plunger is disposed within the inner cavity of the housing and may be movable between a first position and a second position. When the plunger is in the first position, the plunger is free to move translationally away from the opening. While the plunger is in the second position the outwardly extending ridge abuts the inwardly extending step and the forward end abuts the at least one inwardly extending abutment features preventing translational movement of the plunger. Further, a male protuberance interface surface on a rearward end of the plunger may form an air-tight seal between the plunger and the male protrusion when the plunger is in the second position.

The depth stops may be configured so that the shortest possible length of a male luer configuration still enables the plunger to abut the first or second depth stops. As such, the depth stops may allow a consistent travel distance of the cap on every male luer device regardless of luer connector length. This allows consistent dispensing of cleaning solution across all male luers since the translational displacement of the plunger is the same on any male luer and not dependent on the depth of the collar or height of the male protrusion of the male luer.

In one embodiment, the cleaning cap for a medical implement having a male protrusion comprises a housing and a plunger within the housing. The housing has an inner wall that defines an inner cavity and an opening. The housing has a distal end and a proximal end. The opening to the inner cavity is at the proximal end. The plunger is disposed within the inner cavity of the housing. The plunger comprises a rearward end facing the opening and a forward end opposite the rearward end. The plunger comprises a flexible skirt and a protuberance. The flexible skirt extends from the rearward end towards the opening and flares outward to abut the inner wall of the housing. The protuberance is proximate the rearward end of the plunger and extends into the inner cavity of the housing. The protuberance abuts the male protrusion to form an air-tight seal between the plunger and the male protrusion.

An alternative embodiment of the cap includes an annular cut-out defining a flexible tab near the opening of the cap. The flexible tab may enable cleaning solution in the cap to wet the male luer while the plunger is being translationally displaced within the cavity. The flexible tab may then seal against the male luer when the plunger is no longer moving.

The details of one or more embodiments are set forth in the accompanying drawings and the description below. Other features and advantages will be apparent from the description and drawings, and from the claims.

DETAILED DESCRIPTION

The disclosed cap is for placement over a male luer. The cap includes a housing, a movable plunger, and a depth stop for controlling translational displacement of the plunger caused by the male luer. Typically, contained within the cap is a cleaning solution. Movement of the male luer onto the cap moves the plunger and displaces the cleaning solution to protect the male luer from contamination. The depth stop controls movement of the plunger. FIGS. 1-5 show an embodiment of the cap. FIG. 6 shows an embodiment of the cap including a cut-out and flexible tab for allowing cleaning solution to exit an inner cavity of the cap.

Figure 1:
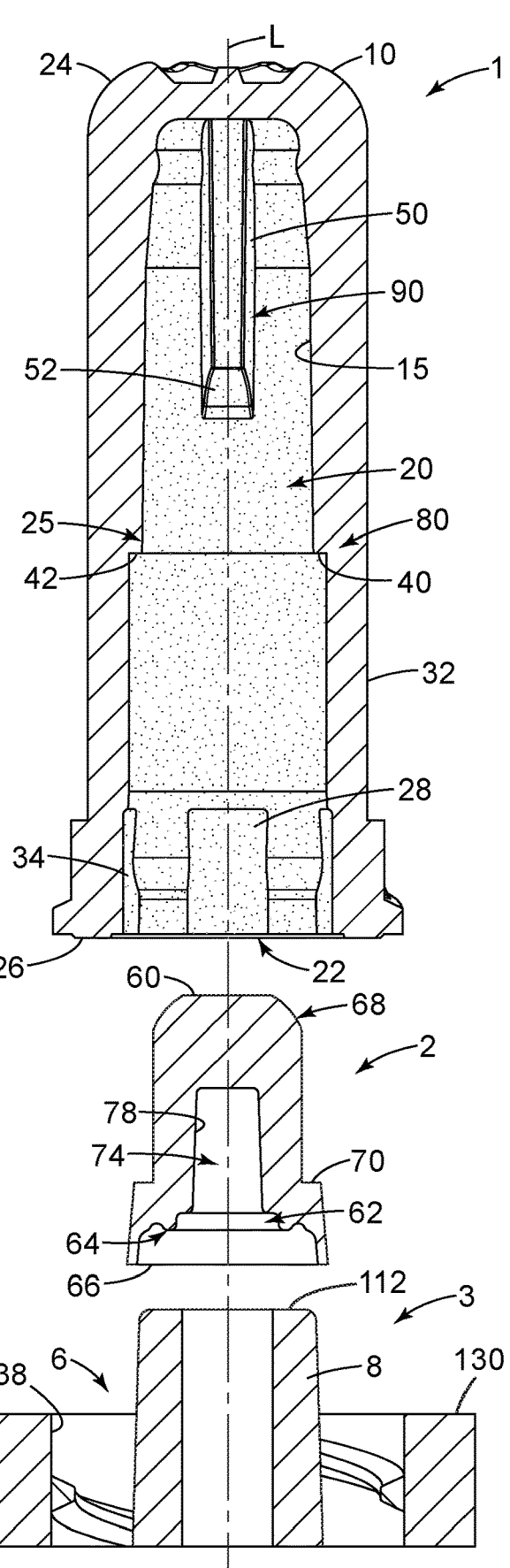
FIG. 1 is an exploded cross-sectional view of a cleaning cap, a plunger, and a medical implement.

FIG. 1 is an exploded cross-sectional view of on embodiment of a cleaning cap 1, a plunger 2 (shown removed from the cap), and a medical implement 3, which is typically a male luer 6 having a male protrusion 8.

The cap 1 includes a housing 10 having an inner wall 15 that defines an inner cavity 20 and an opening 22. The inner cavity 20 has a distal end 24, a proximal end 26, and a medial portion 25 between the distal end 24 and the proximal end 26. The inner cavity 20 is closed on all sides, including the distal end 24, except at the opening 22 at the proximal end 26.

In one embodiment, such as shown in FIG. 1, the housing 10 is cylindrical, and the inner cavity 20 is likewise cylindrical. However, alternative configurations of the housing 10 and inner cavity 20 may be contemplated. For instance, the housing 10 and/or inner cavity 20 may be rectangular, oval, or parallelogrammatic shapes. The housing 10 can have one or more ribs, or ridges, flanges, tabs, etc., for allowing gripping by a user's fingers.

In one embodiment, the inner wall 15 may include one or more vents 28 proximate the opening 22. In some implementations, the vents 28 can be cut-outs, notches or insets at the opening 22, or areas that have an increased diameter than the rest of the opening 22. The vents 28 may be configured to allow a cleaning solution 30 (FIG. 2) to be released from the inner cavity 20 of the cap 1 when the cap 1 is installed on the male luer 6.

An outer surface 32 of the housing 10 may further include one or more threads, protrusions, flanges, or the like, to engage with the threads of a male luer sleeves 38 to retain the cap 1 on the male luer 6. The one or more threads may include at least two partial threads extending from opposite sides of the housing 10 at the opening 22. Alternatively, there may be a single thread extending the entire circumference of the housing 10 near the opening 22. The inner wall 15 may be cylindrical of a substantially uniform diameter, however, toward the opening 22 and proximal end 26 the diameter of the inner wall 15 widens by wider diameter regions with one or more recesses 34, i.e., a maximum diameter of the inner cavity 20, before the diameter narrows again at the diameter of the opening 22. The one or more recesses 34 can also include a recessed inner wall (i.e. large diameter) around the circumference of the inner wall 15 at the recess 34. Alternatively, the one or more recesses 34 can occupy less than the full circumference of the inner wall 15. The recesses 34 may aid in retaining the plunger 2 in a first position prior to being installed on the male luer 6, which will be discussed in greater detail below.

At the medial portion 25 of the inner cavity 20, the inner wall 15 may be inwardly tapered towards a longitudinal axis L and the distal end 24 from the medial portion 25. The longitudinal axis L extends from the proximal end 26 to the distal end 24, and may define a center axis of the cap 1. An annular step 40 may extend from the inner wall 15 towards the longitudinal axis L near the medial portion 25 of the cap 1. The annular step 40 has a first abutment surface 42 that extends towards the longitudinal axis L 360 degrees around the inner wall 15 of the housing 10. The abutment surface 42 extends approximately perpendicular to the inner wall 15, wherein the diameter of the inner cavity 20 is reduced in size. The annular step 40 may represent a diameter of the inner wall 15 that is smaller than a diameter of the plunger 2, which may act as a first depth stop 80 to prevent translational movement of the plunger 2 towards the distal end 24 of the housing 10 when the plunger 2 is in a second position. Extending from the distal end 24 of the inner wall 15 towards the longitudinal axis L may be at least one abutment feature 50. The abutment feature 50 may have an abutment face 52 configured to abut a forward end 60 of the plunger 2, further preventing translational movement of the plunger 2 towards the distal end 24 of the housing 10. The abutment face 52 may extend about 90 degrees from the inner wall 15 towards the longitudinal axis L and may be a planar surface. Alternatively, the abutment face 52 may be an arcuate extension wall configured to accommodate a curved aspect of the forward end 60 of the plunger 2. The abutment feature 50 may act as a second depth stop 90

Figure 2:
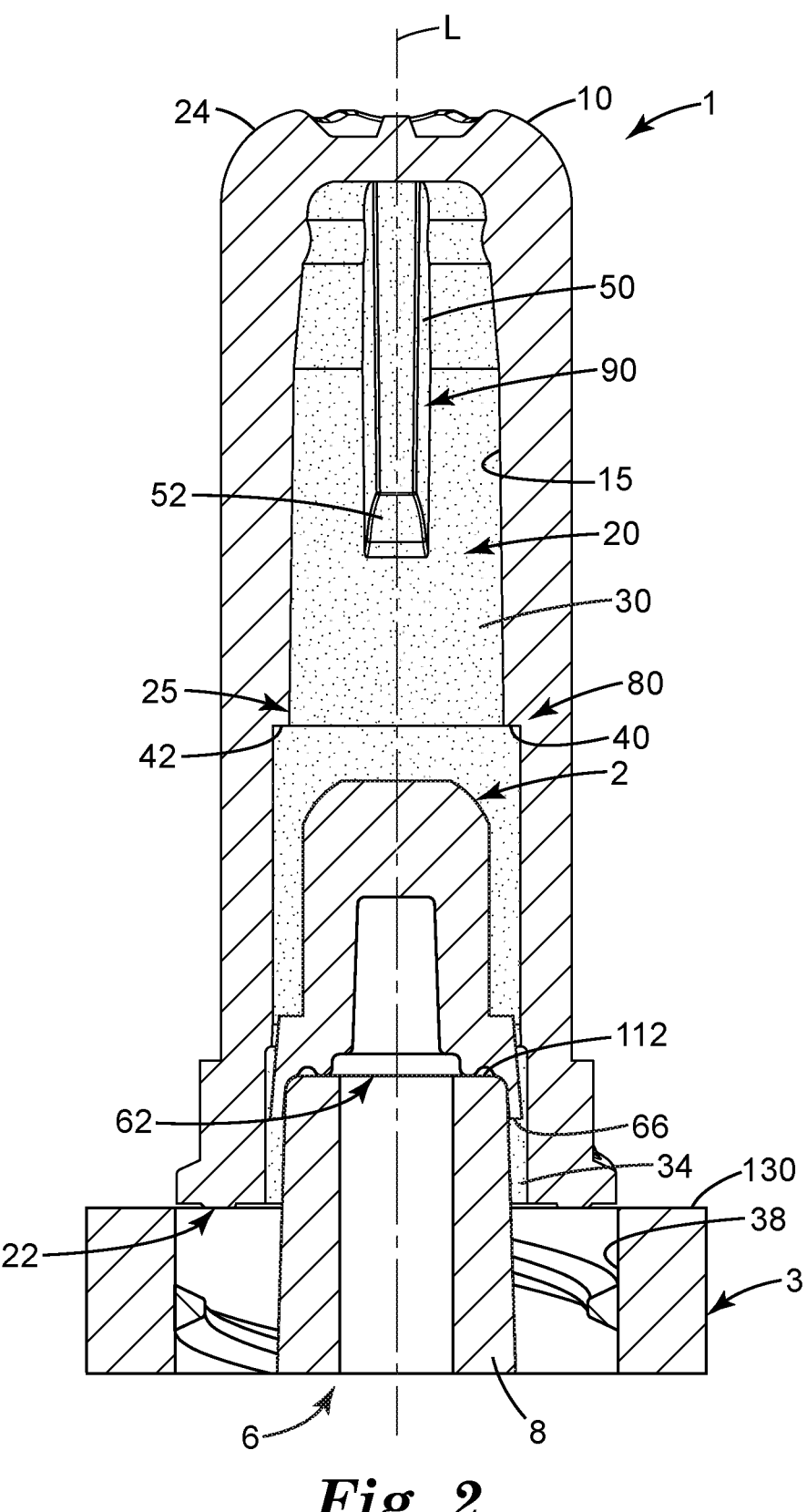
FIG. 2 is a cross-sectional view of the medical implement and the cleaning cap with the plunger in a first position.

The plunger 2 in FIG. 1 is shown removed from the cap 1. However, in assembled form, such as shown in FIG. 2, the plunger is placed in the cap 1. The plunger 2 includes a rearward end 62 that faces the opening 22 of the cap 1 when the plunger 2 resides in the cap 1, and a forward end 60 opposite the rearward end 62 and facing the distal end 24 of the inner cavity 20 (FIG. 2). The plunger 2 may be cylindrical in shape and have a rounded forward end 60 facing the cleaning solution 30. The rearward end 62 may include a protrusion interface surface 64, which will be discussed in further detail below. The forward end 60 may be rounded or pill-shaped to facilitate installation of the plunger 2 within the cap 1. The plunger 2 may additionally include a sealing skirt 66 of flexible material. The sealing skirt 66 is flexible and may be sized to be slightly wider than the recess 34 and the inner wall 15 to hold the plunger 2 against or provide force against the recess 34 and the inner wall 15, which may inhibit movement of the plunger 2 and retain the cleaning solution 30 in the inner cavity 20. The skirt 66 may flare away from the plunger 2 and downward towards the opening 22 at an angle substantially corresponding with a tapering of the wider diameter or tapered diameter region, and to circumscribe some or all of the male protrusion 8 interface surface 64. The sealing skirt 66 may taper towards the longitudinal axis L and the distal end 24. A side wall 68 of the plunger 2 may include an annular ridge 70 that defines an end of the flexible skirt 66. The annular ridge 70 may extend from a side wall 68 of the plunger 2 towards the inner wall 15 of the cap 1 to define a larger diameter of the plunger 2 and the flexible skirt 66. An interior 74 of the plunger 2 may define a plunger cavity 76 defined by a plunger interior wall 78. The interior wall 78 may have a sealing protrusion interface surface 64 near the rearward end 62 configured to engage the male protrusion 8 of the male luer 6 and create an air-tight seal between the plunger 2 and the male luer 6.

Figure 3:
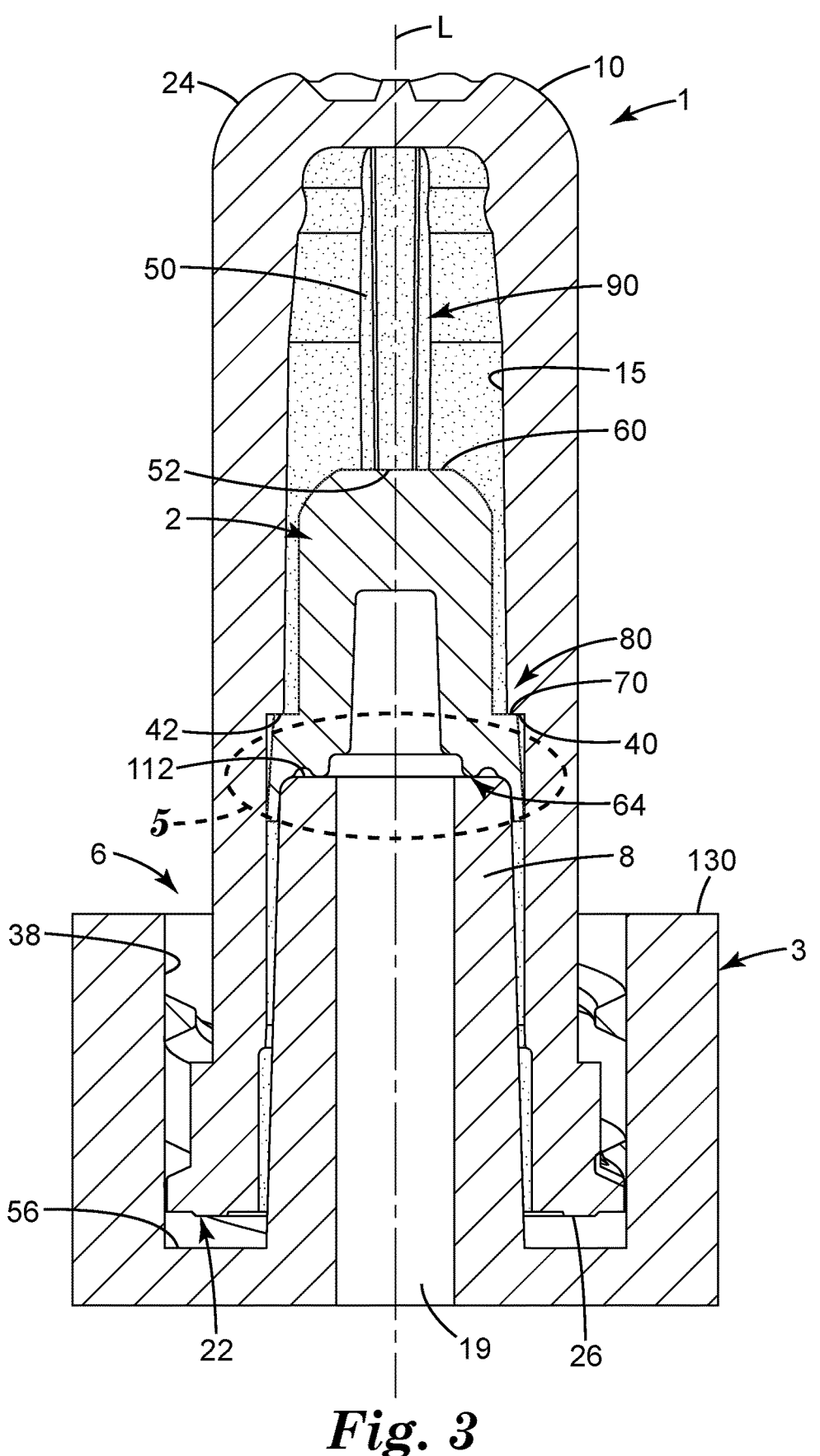
FIG. 3 is a cross-sectional view of the cleaning cap installed on the medical implement, with the plunger in a second position.

Referring to FIGS. 2 and 3, the movable plunger 2 is configured to reside in the inner cavity 20 of the cap 1 and retain a cleaning solution 30 within the inner cavity 20 until the plunger 2 is pushed by the male protrusion 8 of the male luer 6. The plunger 2 may be movable between a first position and a second position.

FIG. 2 illustrates the plunger 2 in the first position, inside of the housing 10 of the cap 1 following insertion of the male protrusion 8 of the male luer 6 and prior to displacement of the plunger 2. While in the first position (FIG. 2), the plunger 2 is in the inner cavity 20 with the rearward end 62 of the plunger 2 proximate the opening 22 and proximal end 26. The recess 34 may accommodate the flexible skirt 66, whereby the flexible skirt 66 may contact the inner wall 15 at the recess 34 preventing movement of the plunger 2 until the plunger 2 is forced out of the first position. Additionally, contact between the flexible skirt 66 and the inner wall 15 may seal the cleaning solution 30 within the inner cavity 20 while the plunger 2 is in the first position. The cleaning solution 30 resides below the plunger 2 in the cap until the plunger 2 is moved by the male luer 6. The cap 1 may then be installed onto the male luer 6 wherein the threads of the cap 1 engage the threads of the male luer 6 to retain the cap 1 on the male luer 6.

As the cap 1 is installed onto the male luer 6, the male protrusion 8 engages the rearward end 62 of the plunger 2 to force it upwards into the inner cavity 20 towards the distal end 24. The plunger 2 is pushed translationally along the direction of the longitudinal axis L within the inner cavity 20 by the male protrusion 8 as the cap 1 is fastened on to the male luer 6. The plunger 2 moves translationally until the plunger 2 engages a first or second depth stop 80, 90 within the inner cavity 20 of the cap 1. Once the plunger 2 has engaged the first or second depth stop 80, 90, the plunger 2 may be retained in the second position from further translational movement towards the distal end 24 (FIG. 3).

FIG. 3 illustrates the male luer 6 inserted into the housing 10 and contacting the plunger 2 via the male protrusion interface surface 64, which may seal a lumen 19 of the male protrusion 8. The contact between the male protrusion 8 and male protrusion interface surface 64 of the plunger 2 will create an air-tight seal between the male protrusion 8 and plunger 2. The air-tight seal prevents 28 cleaning solution 30 from entering the lumen 19 of the male protrusion 8, wherein the cleaning solution takes the path of least resistance and prefers to exit, under pressure from the plunger 2, through the vents 28 as opposed to entering the lumen 19. Additionally, the air-tight seal between the male protrusion 8 and male protrusion interface surface 64 of the plunger 2 may prevent fluid from inside the lumen 19 from escaping the male protrusion 8 and exiting the cap 1 when pressure is applied to a syringe or other medical device.

While in the second position, the plunger 2 is configured to engage at least one depth stop 80, 90 present on the inner wall 15 of the cap 1 in order to prevent translational movement of the plunger 2 towards the distal end 24 of the housing 10.

In one embodiment, the cap 1 includes a first depth stop 80. The first depth stop 80 may include the annular step 40 which may be configured to engage the annular ridge 70 of the plunger 2 at the abutment surface 42. The annular step 40 represents a region of the inner cavity 20 with a diameter less than the diameter of the plunger 2, which prevents the male protrusion 8 or fluid in the lumen 19 from forcing the plunger 2 further into the inner cavity 20. The annular step 40 may extend 360 degrees around the inner wall 15 of the housing 10, or alternatively may include multiple abutment surfaces extending from the inner wall 15, each abutting the annular ridge 70 of the plunger 2 when the plunger 2 is in the second position.

In one embodiment, the cap 1 includes a second depth stop 90. The second depth stop 90 may include the abutment feature 50. The abutment feature 50 may be configured to engage the forward end 60 of the plunger 2 when the plunger 2 is in the second position. The abutment face 52 of the abutment feature 50 may be configured to accommodate the shape and configuration of the forward face of the plunger 2. In some embodiments, the abutment feature 50 may be a single member that extends into the inner cavity 20, or alternatively across the diameter of the cavity. In some other embodiments, there may be multiple abutment features 50 extending from different positions along the inner wall 15 proximate the distal end 24 of the housing 10.

As shown in FIGS. 1-3, the cap 1 may include both the first and second depth stops 80, 90. In which case, the plunger 2 is configured to abut both the first and second depth stops 80, 90 simultaneously when the plunger 2 is in the second position. Alternatively, the cap 1 may include only the first or the second depth stop 80, 90.

The position of the first and second depth stops 80, 90 are based on ISO standards for male luers and are designed to work with the luer 6 and sleeve 38 combination that yields the shortest travel of the plunger 2. Since the diameter across the male luer taper is ISO standard and the luer taper angle is ISO standard, the shortest male protrusion 8 length and shortest sleeve 38 length determine the position of the depth stops 80, 90 from the proximal end 26 of the cap 1. For instance, if the male protrusion 8 is longer or shorter than the sleeves 38 of the male luer 6 the plunger 2 may still contact the first or second depth stop 80, 90 once the cap 1 is fully secured to the medical implement 3. Further, the depth stops 80, 90 are configured to accommodate the shortest possible length of the male luer 6 components. Therefore, the cap 1 ensures that plunger 2 is completely abutted to one of the first or second depth stops 80, 90 while in the second position and that there is an air-tight seal between the male protrusion 8 and the male protrusion interface surface 64 regardless of the length of the male protrusion 8 or the length of the sleeve 38. Further, the position of the depth stops 80, 90 may ensure that the proximal end 26 is prevented from contacting a collar face 56 of the medical implement 3 while the plunger 2 is in the second position. The position of the depth stops 80, 90 ensures that the distance the plunger 2 travels from the first position to the second position remains consistent across all connectors. This also ensures that an equal amount of cleaning solution 30 is applied across a broad range of male luers, ensuring disinfection across multiple designs of male luers. Finally, the depth stops 80, 90 allow the cap 1 to project substantially away from the male luer sleeve towards the distal end 24, such that the cap 1 may be easily installed and uninstalled.

Figure 4:
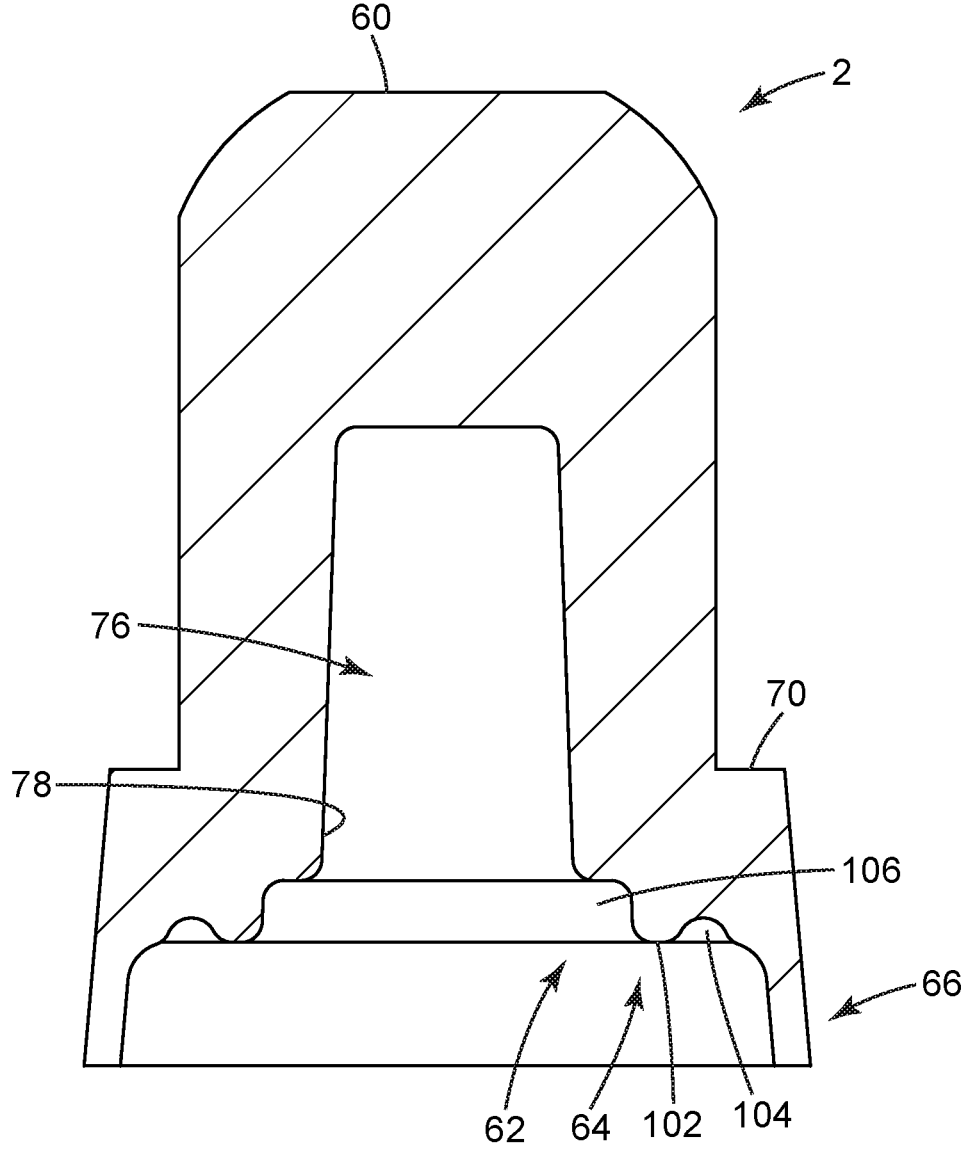
FIG. 4 is an enlarged cross-sectional view of the plunger.

FIG. 4 is a cross-sectional view of the movable plunger 2 that is configured to reside in the cap 1 and retain a cleaning solution 30 within the inner cavity 20 of the housing 10. Movement by the male protrusion 8 of the male luer 6 against the plunger 2 displaces the cleaning solution 30. The plunger 2 may have a rounded or smooth forward end 60 that may be directed toward the distal end 24 of the housing 10. The flexible sealing skirt 66 of the plunger 2 includes a flange 100 which extends downward from the rearward end 62 towards the proximal end 26 of the cap 1 when the plunger 2 resides in the cap 1. An interior plunger wall 78 may define an interior plunger cavity 76 within the plunger 2. The interior plunger wall 78 may additionally define a protrusion interface surface 64 proximate the rearward end 62. The interface surface 64 may include one or more protuberances 102 that extend downwardly from the interior plunger wall 78. Adjacent the protuberance 102 may be one or more gaps 104 and one or more depressions 106 in the interior plunger wall 78.

Figure 5:
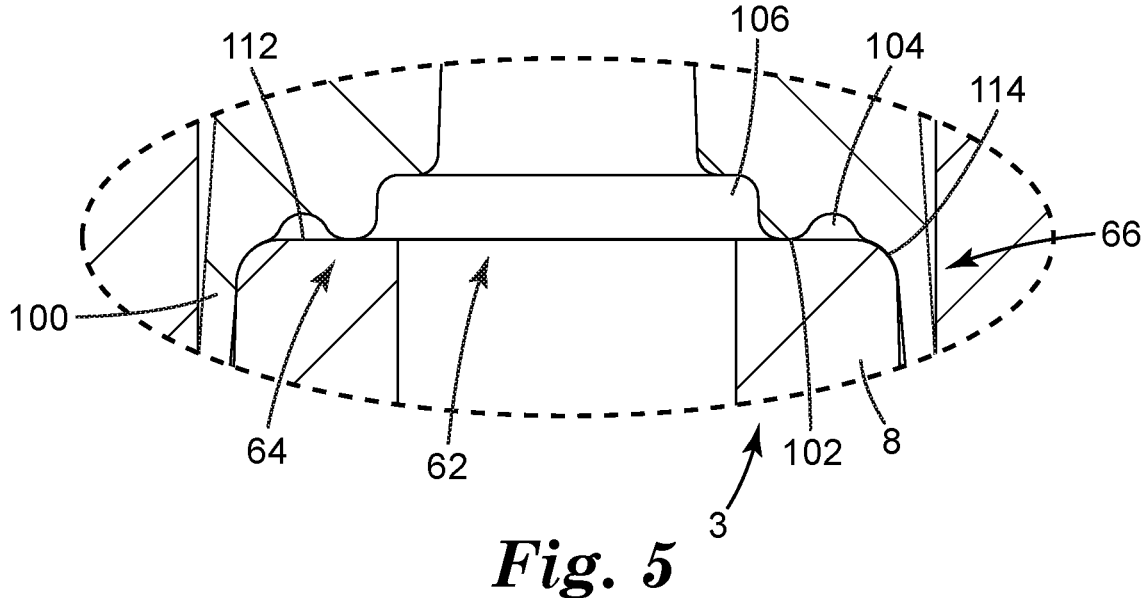
FIG. 5 is an enlarged cross-sectional view of section 5 of FIG. 3.
Figure 6:
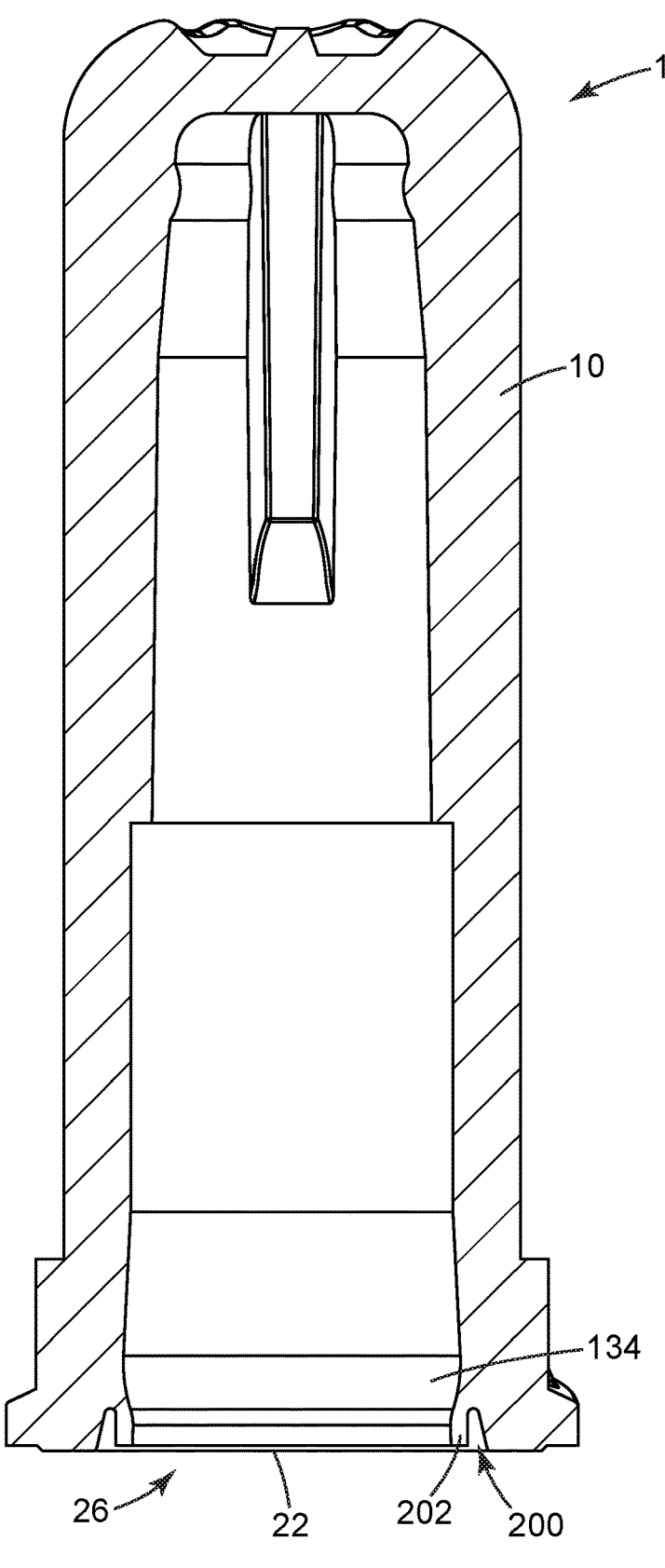
FIG. 6 is a cross-sectional view of an alternative embodiment of the cleaning cap including a cut-out.

FIG. 5 is an enlarged cross-sectional view of the protrusion interface surface 64 of the plunger as it contacts a top surface 112 of the male protrusion 8. As shown in FIG. 5, the protuberance 102 defines a 360 degree sealing surface between the plunger 2 and the male luer 6 when the plunger 2 is in the second position. The protuberance 102 is configured to engage the top surface 112 of the male protrusion 8. A depression 106 having a depth greater than typical mold flash is between the protuberance and the sealing skirt 66 to accommodate surface imperfections such as mold flash that may project from the lumen 19 of the male luer 6. For example, the depth of depression 106 may be between 0.005 to 0.02 inches. The protuberance 102 is generally shown as a projecting member. However, the protuberance 102 may alternatively be a flat piece formed by a two-shot mold at the protrusion interface surface 64. The protuberance 102 may be composed of a softer material to accommodate any surface imperfections or mold flash present on the top surface 112 of the medical implement 3. In this case, a flat two-shot molded polymer layer such as thermoplastic elastomer may be used on top of a flat plunger interface surface 64 as a second layer. As such, the protuberance 102 is capable of deforming to accommodate surface imperfections of the top surface 112, ensuring that a complete air-tight seal between the male protrusion 8 and male protrusion interface surface 64. The air-tight seal between the protuberance 102 and the top surface 112 of the male protrusion 8 ensures that fluid inside of the lumen 19 does not escape the male luer 6 as well as preventing cleaning solution 30 from entering the male luer 6. A second contact point 114 between the flexible skirt 66 of the plunger 2 and the male protrusion 8 may be adjacent to the gap 104.

FIG. 6 is a cross sectional view of an alternative embodiment of the cleaning cap 1 including a cut-out 200. The housing 10 may include a 360 degree cut-out 200 that defines a flexible tab 202 configured to flex when the cap 1 is installed on the male luer 6. The flexible tab 202 and a recess 134 enable the cleaning solution 30 to flow through the opening 22 of the cap 1 and bathe the male luer 6 when the plunger is moved from the first position to the second position. As the cap 1 is installed onto the male luer 6 and the male protrusion 8 forces the plunger 2 further into the cavity 20, the cleaning solution 30 is forced along an exterior side wall of the male protrusion 8 where fluid pressure builds up forcing the flexible tab 202 to flex into the cut-out 200 so that the cleaning solution 30 may flow out of the cap 1 to bathe the rest of the male luer 6. Once the plunger 2 has been moved to the second position, the recess 134 may seal against the walls of the male luer to prevent further ingress or egress of fluids into or out of the cap 1. As such, the flexible tab 202 and recess 134 prevent pressure build up in the cap 1 and prevents cleaning solution 30 from being forced around the cap sealing surface and into the lumen since the path of least resistance is through the opening 22 of the cap. In this way, the cap 1 may be configured without internal vents to allow for the release of cleaning solution 30 from the inner cavity 20 because the cut-out 200 enables the flexible tab 202 to flex to allow cleaning solution 30 to escape the cavity 20.

The cap 1 and plunger 2 can be made from polyethylene or another material that is stable when in the presence of alcohol or other cleaning agent. The cleaning solution 30 can be any chemical, substance or material that cleans the site of bacterial or even viral microorganisms, or any carrier that contains such chemical, substance or material. Examples of a cleaning agent include isopropyl alcohol, chlorohexidine, povidone-iodine, hydrogen peroxide, soap, and hydrochloric acid.

The invention is not limited in its application to the details of construction and the arrangement of components set forth in the description or illustrated in the drawings. The invention is capable of other embodiments and of being practiced or of being carried out in various ways. Also, it is to be understood that the phraseology and terminology used herein is for the purpose of description and should not be regarded as limiting. Terms such as "front," "rear," "top," "bottom," and the like are only used to describe elements as they relate to one another, but are in no way meant to recite specific orientations of the device, to indicate or imply necessary or required orientations of the device, or to specify how the invention described herein will be used, mounted, displayed, or positioned in use. Furthermore, the use of "including," "comprising," or "having" and variations thereof herein is meant to encompass the items listed thereafter and equivalents thereof as well as additional items. Although a few embodiments have been described in detail above, other modifications are possible. Other embodiments may be within the scope of the following claims.

What is claimed is:

1. A cleaning cap for a medical implement having a male protrusion, the cleaning cap comprising:

a housing having an inner wall that defines an inner cavity and an opening, the housing having a distal end and a proximal end;

a plunger disposed within the inner cavity of the housing, wherein the plunger is movable between a first position and a second position;

a depth stop extending from the inner wall at the distal end toward the proximal end within the inner cavity; and wherein at the first position the plunger is free to move translationally away from the opening toward the distal end, and at the second position the plunger abuts the depth stop preventing translational movement of the plunger away from the opening;

wherein the cleaning cap further comprises an annular step extending from the inner wall toward the inner cavity.

2. The cleaning cap of claim 1, wherein the depth stop comprises an abutment face configured to abut the plunger when the plunger is in the second position.

3. The cleaning cap of claim 1, wherein the plunger comprises an annular ridge, and wherein the annular step is configured to abut the annular ridge when the plunger is in the second position.

4. The cleaning cap of claim 1, wherein the housing contains a cleaning solution, and wherein movement of the plunger toward the second position by the male protrusion forces the cleaning solution into contact with an outer wall of the male protrusion.

5. The cleaning cap of claim 1, wherein the depth stop extends along a central longitudinal axis of the housing.

6. A cleaning cap for a medical implement having a male protrusion, the cleaning cap comprising:

a housing having an inner wall that defines an inner cavity, an opening, and a step extending from the inner wall; and a plunger disposed within the inner cavity of the housing, wherein the plunger is movable between a first position and a second position, and wherein the plunger comprises a ridge;

wherein at the first position, the plunger is free to move translationally away from the opening;

wherein at the second position, the ridge abuts the step, thereby preventing translational movement of the plunger away from the opening; and wherein the ridge is an annular ridge and the step is an annular step.

7. The cleaning cap of claim 6, wherein a cleaning solution is retained within the inner cavity of the housing, and wherein translational movement of the plunger toward the second position forces the cleaning solution into contact with an outer wall of the male protrusion.

8. The cleaning cap of claim 7, further comprising a plurality of vents disposed along the inner wall, wherein the cleaning solution is directed along an outer wall of the male protrusion when the plunger is moved from the first position toward the second position.

9. The cleaning cap of claim 7, wherein the housing defines a flexible tab that flexes to release a cleaning solution from the inner cavity when the plunger is moved from the first position toward the second position.

10. The cleaning cap of claim 6, wherein the inner cavity includes a first portion exhibiting a first width and a second portion exhibiting a second width different than the first width, and wherein the annular step is located between the first and second portions.

11. The cleaning cap of claim 6, wherein the housing comprises a proximal end and a distal end, and wherein the ridge is located between the proximal and distal ends.

12. A cleaning cap for a medical implement having a male protrusion, the cleaning cap comprising:

a housing having an inner wall that defines an inner cavity and an opening;

a plunger disposed within the inner cavity of the housing, wherein the plunger is movable between a first position and a second position, wherein the plunger provides an interior wall that includes a protuberance that extends toward the opening, wherein the protuberance defines one or more gaps in the interior wall, and wherein the protuberance is configured to be engaged by the male protrusion to create an air-tight seal between the plunger and the medical implement; and a cleaning solution retained within the inner cavity of the housing, and wherein translational movement of the plunger toward the second position forces the cleaning solution into contact with an outer wall of the male protrusion.

13. The cleaning cap of claim 12, wherein the protuberance is deformable to accommodate surface imperfections of a top surface of the male protrusion.

14. The cleaning cap of claim 12, wherein the air-tight seal prevents the cleaning solution from entering the male protrusion as the plunger toward the second position.

15. The cleaning cap of claim 12, wherein the plunger comprises a flexible skirt including a flange extending toward the opening.

16. The cleaning cap of claim 12, wherein the housing further provides a step extending from the inner wall, wherein the plunger provides a ridge, and wherein, wherein at the second position, the ridge abuts the step, thereby preventing translational movement of the plunger away from the opening.

17. The cleaning cap of claim 12, wherein the housing provides a depth stop extending along a central longitudinal axis of the housing, and wherein, in the second position, the plunger abuts the depth stop, thereby preventing translational movement of the plunger away from the opening.

* * * * *